United States Patent
Quintanar

(10) Patent No.: US 11,160,915 B2
(45) Date of Patent: Nov. 2, 2021

(54) REDUNDANT CONTROLS FOR NEGATIVE PRESSURE WOUND THERAPY SYSTEMS

(71) Applicant: Smith & Nephew PLC, Watford (GB)

(72) Inventor: Felix Clarence Quintanar, Hull (GB)

(73) Assignee: Smith & Nephew PLC, Watford (GB)

( * ) Notice: Subject to any disclaimer, the term of this patent is extended or adjusted under 35 U.S.C. 154(b) by 122 days.

(21) Appl. No.: 16/609,363

(22) PCT Filed: May 4, 2018

(86) PCT No.: PCT/EP2018/061476
§ 371 (c)(1),
(2) Date: Oct. 29, 2019

(87) PCT Pub. No.: WO2018/206420
PCT Pub. Date: Nov. 15, 2018

(65) Prior Publication Data
US 2020/0086013 A1    Mar. 19, 2020

Related U.S. Application Data

(60) Provisional application No. 62/503,697, filed on May 9, 2017.

(51) Int. Cl.
*A61M 1/00* (2006.01)
*H01H 9/54* (2006.01)
(Continued)

(52) U.S. Cl.
CPC ............ *A61M 1/742* (2021.05); *A61M 1/743* (2021.05); *A61M 1/84* (2021.05); *H01H 9/16* (2013.01);
(Continued)

(58) Field of Classification Search
CPC .. A61M 1/0033; A61M 1/0035; A61M 1/008; A61M 2205/6027; A61M 2205/17;
(Continued)

(56) References Cited

U.S. PATENT DOCUMENTS 3,874,387 A    4/1975    Barbieri
4,224,941 A    9/1980    Stivala
(Continued)

FOREIGN PATENT DOCUMENTS

CN    201664463 U    12/2010
DE    198 44 355    4/2000
(Continued)

OTHER PUBLICATIONS

International Search Report and Written Opinion, re PCT Application No. PCT/EP2018/061476, dated Aug. 20, 2018.
(Continued)

*Primary Examiner* — Nicholas J Weiss
*Assistant Examiner* — Eric Rassavong
(74) *Attorney, Agent, or Firm* — Knobbe, Martens, Olson & Bear, LLP

(57) ABSTRACT

Embodiments of negative pressure wound therapy systems and methods are disclosed. In one embodiment, a system includes a wound dressing, negative pressure source, switch, and control circuitry. The switch can include an actuator that toggles states of first and second pairs of contacts in response to a user input. The control circuitry can supply negative pressure with the negative pressure source when the state of the first pair of contacts is a first state and the state of the second pair of contacts is a second state, and the control circuitry can disable supply of negative pressure with the negative pressure source when the state of the first pair of contacts is not the first state or the state of the second pair of contacts is not the second state.

20 Claims, 9 Drawing Sheets

(51) Int. Cl.
  *H01H 9/00* (2006.01)
  *H01H 9/16* (2006.01)
(52) U.S. Cl.
  CPC ........... *H01H 9/54* (2013.01); *A61M 2205/13* (2013.01); *A61M 2205/3344* (2013.01); *A61M 2205/502* (2013.01); *A61M 2205/587* (2013.01); *A61M 2205/6027* (2013.01); *H01H 2009/0083* (2013.01)
(58) Field of Classification Search
  CPC ................. A61M 1/0031; H01H 9/54; H01H 2009/0083
  See application file for complete search history.

(56) References Cited

U.S. PATENT DOCUMENTS

| | | | |
|---|---|---|---|
| 4,398,910 A | 8/1983 | Blake et al. | |
| 4,534,356 A | 8/1985 | Papadakis | |
| 4,569,674 A | 2/1986 | Phillips | |
| 4,624,656 A | 11/1986 | Clark et al. | |
| 4,681,562 A | 7/1987 | Beck et al. | |
| 4,767,943 A | 8/1988 | Adler et al. | |
| 4,979,944 A | 12/1990 | Luzsicza | |
| 5,055,195 A | 10/1991 | Trasch et al. | |
| 5,055,198 A | 10/1991 | Shettigar | |
| 5,056,510 A | 10/1991 | Gilman | |
| 5,152,757 A | 10/1992 | Eriksson | |
| 5,181,905 A | 1/1993 | Flam | |
| 5,266,928 A | 11/1993 | Johnson | |
| D357,743 S | 4/1995 | Bilitz et al. | |
| 5,527,293 A | 6/1996 | Zamierowski | |
| 5,549,584 A | 8/1996 | Gross | |
| 5,636,643 A | 6/1997 | Argenta et al. | |
| 5,643,189 A | 7/1997 | Masini | |
| 5,779,657 A | 7/1998 | Daneshvar | |
| 5,833,646 A | 11/1998 | Masini | |
| 5,902,256 A | 5/1999 | Benaron | |
| 5,964,723 A | 10/1999 | Augustine | |
| 6,071,267 A | 6/2000 | Zamierowski | |
| 6,142,982 A | 11/2000 | Hunt et al. | |
| 6,168,800 B1 | 1/2001 | Dobos et al. | |
| 6,183,438 B1 | 2/2001 | Berguer | |
| 6,225,523 B1 | 5/2001 | Masini | |
| 6,261,276 B1 | 7/2001 | Reitsma | |
| 6,261,283 B1 | 7/2001 | Morgan et al. | |
| 6,398,767 B1 | 6/2002 | Fleischmann | |
| 6,458,109 B1 | 10/2002 | Henley et al. | |
| 6,471,982 B1 | 10/2002 | Lydon et al. | |
| 6,599,262 B1 | 7/2003 | Masini | |
| 6,607,495 B1 | 8/2003 | Skalak et al. | |
| 6,685,681 B2 | 2/2004 | Lockwood et al. | |
| 6,787,682 B2 | 9/2004 | Gilman | |
| 6,794,554 B2 | 9/2004 | Sessions et al. | |
| 6,800,074 B2 | 10/2004 | Henley et al. | |
| 6,855,135 B2 | 2/2005 | Lockwood et al. | |
| 6,942,633 B2 | 9/2005 | Odland | |
| 6,951,553 B2 | 10/2005 | Bubb et al. | |
| 6,979,324 B2 | 12/2005 | Bybordi et al. | |
| 7,004,915 B2 | 2/2006 | Boynton et al. | |
| 7,022,113 B2 | 4/2006 | Lockwood et al. | |
| 7,067,709 B2 | 6/2006 | Murata et al. | |
| 7,070,584 B2 | 7/2006 | Johnson et al. | |
| 7,087,806 B2 | 8/2006 | Scheinberg et al. | |
| 7,108,683 B2 | 9/2006 | Zamierowski | |
| 7,216,651 B2 | 5/2007 | Argenta et al. | |
| 7,338,482 B2 | 3/2008 | Lockwood et al. | |
| 7,361,184 B2 | 4/2008 | Joshi | |
| 7,524,315 B2 | 4/2009 | Blott et al. | |
| 7,553,306 B1 | 6/2009 | Hunt et al. | |
| 7,569,742 B2 | 8/2009 | Haggstrom et al. | |
| 7,611,500 B1 | 11/2009 | Lina et al. | |
| 7,615,036 B2 | 11/2009 | Joshi et al. | |
| D605,775 S | 12/2009 | Koch et al. | |
| D608,007 S | 1/2010 | Arbesman et al. | |
| 7,645,253 B2 | 1/2010 | Gura et al. | |
| 7,687,678 B2 | 3/2010 | Jacobs | |
| 7,699,823 B2 | 4/2010 | Haggstrom et al. | |
| 7,776,028 B2 | 8/2010 | Miller et al. | |
| 7,779,625 B2 | 8/2010 | Joshi et al. | |
| D625,422 S | 10/2010 | Arbesman et al. | |
| 7,837,673 B2 | 11/2010 | Vogel | |
| 7,838,717 B2 | 11/2010 | Haggstrom et al. | |
| 7,846,141 B2 | 12/2010 | Weston | |
| 7,896,864 B2 | 3/2011 | Lockwood et al. | |
| 7,922,676 B2 | 4/2011 | Daskal et al. | |
| 7,922,703 B2 | 4/2011 | Riesinger | |
| 7,942,866 B2 | 5/2011 | Radl et al. | |
| 7,959,624 B2 | 6/2011 | Riesinger | |
| 7,976,519 B2 | 7/2011 | Bubb et al. | |
| 8,007,257 B2 | 8/2011 | Heaton et al. | |
| 8,007,481 B2 | 8/2011 | Schuessler et al. | |
| 8,062,272 B2 | 11/2011 | Weston | |
| 8,062,273 B2 | 11/2011 | Weston | |
| 8,080,702 B2 | 12/2011 | Blott et al. | |
| 8,092,441 B2 | 1/2012 | Sugito | |
| 8,118,794 B2 | 2/2012 | Weston et al. | |
| 8,158,844 B2 | 4/2012 | McNeil | |
| 8,167,869 B2 | 5/2012 | Wudyka | |
| 8,207,392 B2 | 6/2012 | Haggstrom et al. | |
| 8,212,100 B2 | 7/2012 | Moore | |
| 8,215,929 B2 | 7/2012 | Shen et al. | |
| 8,323,264 B2 | 12/2012 | Weston et al. | |
| 8,371,829 B2 | 2/2013 | Jaeb et al. | |
| 8,372,049 B2 | 2/2013 | Jaeb et al. | |
| 8,372,050 B2 | 2/2013 | Jaeb et al. | |
| 8,404,921 B2 | 3/2013 | Lee et al. | |
| 8,409,157 B2 | 4/2013 | Haggstrom et al. | |
| 8,409,160 B2 | 4/2013 | Locke et al. | |
| 8,414,519 B2 | 4/2013 | Hudspeth et al. | |
| 8,419,696 B2 | 4/2013 | Wilkes | |
| 8,425,478 B2 | 4/2013 | Olson | |
| 8,439,894 B1 | 5/2013 | Miller | |
| 8,444,612 B2 | 5/2013 | Patel et al. | |
| 8,449,508 B2 | 5/2013 | Coulthard et al. | |
| 8,460,255 B2 | 6/2013 | Joshi et al. | |
| 8,500,776 B2 | 8/2013 | Ebner | |
| 8,529,548 B2 | 9/2013 | Blott et al. | |
| 8,545,464 B2 | 10/2013 | Weston | |
| 8,545,466 B2 | 10/2013 | Andresen et al. | |
| 8,569,566 B2 | 10/2013 | Blott et al. | |
| 8,579,872 B2 | 11/2013 | Coulthard et al. | |
| 8,603,074 B2 | 12/2013 | Kagan | |
| 8,604,265 B2 | 12/2013 | Locke et al. | |
| 8,628,505 B2 | 1/2014 | Weston | |
| 8,641,691 B2 | 2/2014 | Fink | |
| 8,641,693 B2 | 2/2014 | Locke et al. | |
| 8,702,665 B2 | 4/2014 | Locke et al. | |
| 8,764,732 B2 | 7/2014 | Hartwell | |
| 8,795,257 B2 | 8/2014 | Coulthard et al. | |
| 8,808,274 B2 | 8/2014 | Hartwell | |
| 8,814,842 B2 | 8/2014 | Coulthard et al. | |
| 8,821,458 B2 | 9/2014 | Locke et al. | |
| 8,829,263 B2 | 9/2014 | Haggstrom et al. | |
| 8,870,837 B2 | 10/2014 | Locke et al. | |
| 8,915,895 B2 | 12/2014 | Jaeb et al. | |
| 8,961,496 B2 | 2/2015 | Locke et al. | |
| 8,974,429 B2 | 3/2015 | Gordon et al. | |
| 9,050,209 B2 | 6/2015 | Coulthard et al. | |
| 9,061,095 B2 | 6/2015 | Adie et al. | |
| 9,084,845 B2 | 7/2015 | Adie et al. | |
| 9,089,630 B2 | 7/2015 | Perkins et al. | |
| 9,168,330 B2 | 10/2015 | Joshi et al. | |
| 9,198,802 B2 | 12/2015 | Robinson et al. | |
| 9,220,822 B2 | 12/2015 | Hartwell et al. | |
| 9,259,558 B2 | 2/2016 | Tsai | |
| 9,265,665 B2 | 2/2016 | Robinson et al. | |
| 9,265,867 B2 | 2/2016 | Coulthard et al. | |
| 9,283,118 B2 | 3/2016 | Locke et al. | |
| 9,393,354 B2 | 7/2016 | Freedman et al. | |
| 9,414,968 B2 | 8/2016 | Heagle | |
| 9,421,133 B2 | 8/2016 | Hu et al. | |
| 9,427,505 B2 | 8/2016 | Askem et al. | |
| 9,446,176 B2 | 9/2016 | Locke et al. | |

(56) References Cited

U.S. PATENT DOCUMENTS

| | | |
|---|---|---|
| 9,452,088 B2 | 9/2016 | Shulman et al. |
| 9,452,245 B2 | 9/2016 | Jaeb et al. |
| 9,560,975 B2 | 2/2017 | Mei et al. |
| 9,629,986 B2 | 4/2017 | Patel et al. |
| D787,690 S | 5/2017 | Mackay et al. |
| 9,669,138 B2 | 6/2017 | Joshi et al. |
| 9,737,649 B2 | 8/2017 | Begin et al. |
| 9,770,368 B2 | 9/2017 | Robinson et al. |
| 9,795,725 B2 | 10/2017 | Joshi et al. |
| 9,814,811 B2 | 11/2017 | Aalders et al. |
| 9,844,475 B2 | 12/2017 | Hartwell |
| 9,907,703 B2 | 3/2018 | Allen et al. |
| 9,925,092 B2 | 3/2018 | Luckemeyer et al. |
| RE46,778 E | 4/2018 | Peron |
| 9,956,120 B2 | 5/2018 | Locke |
| 10,004,914 B2 | 6/2018 | Nettesheim et al. |
| 10,010,656 B2 | 7/2018 | Jaeb et al. |
| 10,016,309 B2 | 7/2018 | Hartwell |
| 10,016,544 B2 | 7/2018 | Coulthard et al. |
| 10,046,095 B1 | 8/2018 | Middaugh et al. |
| 10,046,096 B2 | 8/2018 | Askem et al. |
| 10,086,117 B2 | 10/2018 | Locke et al. |
| 10,123,909 B2 | 11/2018 | Hartwell |
| 10,201,644 B2 | 2/2019 | Haggstrom et al. |
| 10,265,445 B2 | 4/2019 | Weston |
| 10,384,041 B2 | 8/2019 | Patel et al. |
| 10,391,212 B2 | 8/2019 | Joshi et al. |
| 2003/0212357 A1 | 11/2003 | Pace |
| 2004/0064132 A1 | 4/2004 | Boehringer et al. |
| 2004/0076662 A1 | 4/2004 | Riesinger |
| 2004/0087884 A1 | 5/2004 | Haddock et al. |
| 2004/0167482 A1 | 8/2004 | Watson |
| 2005/0012616 A1 | 1/2005 | Forster et al. |
| 2005/0045461 A1* | 3/2005 | Sweetland ............... H01H 1/38 200/275 |
| 2005/0065471 A1 | 3/2005 | Kuntz |
| 2005/0119737 A1 | 6/2005 | Bene et al. |
| 2005/0131327 A1 | 6/2005 | Lockwood et al. |
| 2005/0137539 A1 | 6/2005 | Biggie et al. |
| 2006/0029650 A1 | 2/2006 | Coffey |
| 2006/0086598 A1 | 4/2006 | Sneek et al. |
| 2006/0107642 A1 | 5/2006 | Smith et al. |
| 2006/0213527 A1 | 9/2006 | Argenta et al. |
| 2006/0259102 A1 | 11/2006 | Slatkine |
| 2007/0055209 A1 | 3/2007 | Patel et al. |
| 2007/0128055 A1 | 6/2007 | Lee |
| 2007/0179460 A1 | 8/2007 | Adahan |
| 2007/0225663 A1 | 9/2007 | Watt et al. |
| 2007/0255187 A1 | 11/2007 | Branch |
| 2008/0021356 A1 | 1/2008 | Castello Escude et al. |
| 2008/0051716 A1 | 2/2008 | Stutz |
| 2009/0012484 A1 | 1/2009 | Nielsen et al. |
| 2009/0048556 A1 | 2/2009 | Durand |
| 2010/0022990 A1 | 1/2010 | Karpowicz et al. |
| 2010/0100160 A2 | 4/2010 | Edman et al. |
| 2010/0137775 A1 | 6/2010 | Hu et al. |
| 2010/0160881 A1 | 6/2010 | Lin et al. |
| 2010/0280469 A1 | 11/2010 | Hall |
| 2010/0292632 A1 | 11/2010 | Mulvihill et al. |
| 2011/0092927 A1 | 4/2011 | Wilkes et al. |
| 2011/0112492 A1 | 5/2011 | Bharti et al. |
| 2011/0224631 A1 | 9/2011 | Simmons |
| 2011/0292623 A1 | 12/2011 | Stanley |
| 2011/0305736 A1 | 12/2011 | Wieland et al. |
| 2012/0059294 A1 | 3/2012 | Schubert et al. |
| 2012/0109034 A1 | 5/2012 | Locke et al. |
| 2013/0090615 A1 | 4/2013 | Jaeb et al. |
| 2013/0102979 A1 | 4/2013 | Coulthard et al. |
| 2013/0215638 A1 | 8/2013 | Dabov et al. |
| 2014/0100536 A1 | 4/2014 | Angel |
| 2014/0330227 A1 | 11/2014 | Coulthard et al. |
| 2014/0343518 A1 | 11/2014 | Riesinger |
| 2015/0057625 A1 | 2/2015 | Coulthard et al. |
| 2015/0174304 A1* | 6/2015 | Askem .................. A61M 1/009 604/319 |
| 2015/0202354 A1 | 7/2015 | Wall |
| 2015/0258256 A1 | 9/2015 | Jaeb et al. |
| 2015/0250931 A1 | 10/2015 | Bharti et al. |
| 2016/0015873 A1 | 1/2016 | Robinson et al. |
| 2016/0166438 A1 | 6/2016 | Rovaniemi |
| 2016/0199546 A1 | 7/2016 | Chao |
| 2016/0206793 A1 | 7/2016 | Robinson et al. |
| 2016/0242964 A1 | 8/2016 | Rapp et al. |
| 2016/0271305 A1 | 9/2016 | Kurihara et al. |
| 2016/0361473 A1 | 12/2016 | Robinson et al. |
| 2017/0014556 A1 | 1/2017 | Haggstrom et al. |
| 2017/0112974 A1 | 4/2017 | Fujisaki |
| 2017/0112975 A1 | 4/2017 | Fujisaki |
| 2017/0127525 A1 | 5/2017 | Schonholz |
| 2017/0232189 A1 | 8/2017 | Qin et al. |
| 2017/0296714 A1 | 10/2017 | Locke et al. |
| 2017/0304510 A1 | 10/2017 | Askem et al. |
| 2017/0319761 A1 | 11/2017 | Locke et al. |
| 2017/0326277 A1 | 11/2017 | Huang |
| 2018/0008760 A1 | 1/2018 | Zilbershlag et al. |
| 2018/0021178 A1 | 1/2018 | Locke et al. |
| 2018/0028728 A1 | 2/2018 | Aarestad et al. |
| 2018/0104393 A1 | 4/2018 | Wu et al. |
| 2018/0200414 A1 | 7/2018 | Askem et al. |
| 2018/0272052 A1 | 9/2018 | Locke et al. |
| 2018/0296397 A1 | 10/2018 | Askem et al. |
| 2018/0311078 A1 | 11/2018 | Hartwell |
| 2018/0318137 A1 | 11/2018 | Donda et al. |
| 2018/0318165 A1 | 11/2018 | Donda et al. |
| 2018/0353771 A1 | 12/2018 | Kim et al. |
| 2019/0021911 A1 | 1/2019 | Askem et al. |
| 2019/0091381 A1 | 3/2019 | Askem et al. |
| 2019/0125943 A1 | 5/2019 | Askem et al. |
| 2019/0142644 A1 | 5/2019 | Askem et al. |
| 2019/0142647 A1 | 5/2019 | Hartwell |
| 2019/0143007 A1 | 5/2019 | Askem et al. |
| 2019/0159938 A1 | 5/2019 | Askem et al. |
| 2019/0192350 A1 | 6/2019 | Gowans et al. |

FOREIGN PATENT DOCUMENTS

| | | |
|---|---|---|
| EP | 0 512 543 | 11/1992 |
| EP | 1411874 A1 | 4/2004 |
| EP | 1455701 B1 | 3/2006 |
| EP | 1807032 A1 | 7/2007 |
| EP | 1476217 B1 | 3/2008 |
| EP | 1976477 A2 | 10/2008 |
| EP | 1507498 B1 | 7/2009 |
| EP | 1791579 B1 | 7/2009 |
| EP | 2109472 A1 | 10/2009 |
| EP | 1947987 B1 | 5/2010 |
| EP | 1358456 B1 | 7/2010 |
| EP | 2214728 A2 | 8/2010 |
| EP | 2279016 A1 | 2/2011 |
| EP | 2340064 A1 | 7/2011 |
| EP | 2346468 A2 | 7/2011 |
| EP | 2349155 A2 | 8/2011 |
| EP | 2205190 B1 | 9/2011 |
| EP | 2370116 A2 | 10/2011 |
| EP | 2531761 A1 | 12/2012 |
| EP | 2231088 B1 | 1/2013 |
| EP | 2015655 B1 | 3/2013 |
| EP | 2285323 B1 | 3/2013 |
| EP | 2563421 A1 | 3/2013 |
| EP | 2049055 B1 | 4/2013 |
| EP | 2340066 B1 | 4/2013 |
| EP | 2440260 B1 | 5/2013 |
| EP | 2 603 699 | 6/2013 |
| EP | 2340062 B1 | 6/2013 |
| EP | 1893145 B1 | 7/2013 |
| EP | 2370142 B1 | 7/2013 |
| EP | 2279017 B1 | 8/2013 |
| EP | 2370117 B1 | 8/2013 |
| EP | 2258443 B1 | 9/2013 |
| EP | 2659915 A1 | 11/2013 |
| EP | 1848390 B1 | 12/2013 |
| EP | 1875081 B1 | 12/2013 |
| EP | 2271381 B1 | 12/2013 |
| EP | 2160166 B1 | 1/2014 |

(56) References Cited

FOREIGN PATENT DOCUMENTS

| | | |
|---|---|---|
| EP | 1565219 B1 | 2/2014 |
| EP | 2 345 437 | 4/2014 |
| EP | 2305325 B1 | 4/2014 |
| EP | 2323712 B1 | 4/2014 |
| EP | 2451498 B1 | 4/2014 |
| EP | 2051675 B1 | 6/2014 |
| EP | 1485613 B1 | 7/2014 |
| EP | 1545644 B1 | 8/2014 |
| EP | 2349154 B1 | 8/2014 |
| EP | 2146759 B1 | 9/2014 |
| EP | 2416816 B1 | 10/2014 |
| EP | 2468323 B1 | 10/2014 |
| EP | 2658493 B1 | 10/2014 |
| EP | 1850818 B1 | 12/2014 |
| EP | 2268348 B1 | 12/2014 |
| EP | 2561128 B1 | 1/2015 |
| EP | 2829287 A1 | 1/2015 |
| EP | 2683285 B1 | 2/2015 |
| EP | 2470136 B1 | 3/2015 |
| EP | 2503974 B1 | 5/2015 |
| EP | 2249894 B1 | 8/2015 |
| EP | 2802366 B1 | 8/2015 |
| EP | 2438302 B1 | 9/2015 |
| EP | 2346545 B1 | 10/2015 |
| EP | 2438301 B1 | 10/2015 |
| EP | 2802304 B1 | 12/2015 |
| EP | 2852421 B1 | 1/2016 |
| EP | 2410962 B1 | 3/2016 |
| EP | 2640436 B1 | 3/2016 |
| EP | 2855937 B1 | 5/2016 |
| EP | 2433594 B1 | 6/2016 |
| EP | 2919730 B1 | 6/2016 |
| EP | 2861869 B1 | 7/2016 |
| EP | 2945584 B1 | 7/2016 |
| EP | 2293749 B1 | 8/2016 |
| EP | 3 072 542 | 9/2016 |
| EP | 2305327 B1 | 10/2016 |
| EP | 2467086 B1 | 10/2016 |
| EP | 2470135 B1 | 10/2016 |
| EP | 2767305 B1 | 10/2016 |
| EP | 2282788 B1 | 12/2016 |
| EP | 2462956 B2 | 3/2017 |
| EP | 3139878 A1 | 3/2017 |
| EP | 2249761 B1 | 4/2017 |
| EP | 1587502 B1 | 5/2017 |
| EP | 1587554 B1 | 5/2017 |
| EP | 2731563 B1 | 5/2017 |
| EP | 2968871 B1 | 7/2017 |
| EP | 3 062 751 | 8/2017 |
| EP | 2632613 B1 | 8/2017 |
| EP | 2888478 B1 | 8/2017 |
| EP | 2937107 B1 | 8/2017 |
| EP | 2967627 B1 | 8/2017 |
| EP | 3139879 B1 | 8/2017 |
| EP | 2359784 B1 | 9/2017 |
| EP | 3151795 B1 | 9/2017 |
| EP | 2367518 B1 | 10/2017 |
| EP | 2675493 B1 | 10/2017 |
| EP | 3068455 B1 | 10/2017 |
| EP | 2558046 B2 | 11/2017 |
| EP | 2736548 B1 | 11/2017 |
| EP | 3052158 B1 | 11/2017 |
| EP | 3 257 486 | 12/2017 |
| EP | 2593058 B1 | 3/2018 |
| EP | 3139880 B1 | 3/2018 |
| EP | 1496822 B1 | 8/2018 |
| EP | 2879633 B1 | 8/2018 |
| EP | 2227203 B1 | 9/2018 |
| EP | 2696826 B1 | 9/2018 |
| EP | 3106186 B1 | 9/2018 |
| EP | 3162330 B1 | 9/2018 |
| EP | 3169382 B1 | 9/2018 |
| EP | 3203953 B1 | 9/2018 |
| EP | 2941280 B1 | 10/2018 |
| EP | 3244852 B1 | 10/2018 |
| EP | 2687241 B2 | 11/2018 |
| EP | 3062753 B1 | 11/2018 |
| EP | 3120879 B1 | 12/2018 |
| EP | 3191149 B1 | 1/2019 |
| EP | 2370130 B1 | 3/2019 |
| EP | 3053609 B1 | 3/2019 |
| EP | 3180048 B1 | 3/2019 |
| EP | 3143974 B1 | 4/2019 |
| EP | 2285432 B2 | 6/2019 |
| EP | 3050545 B1 | 7/2019 |
| EP | 3319656 B1 | 8/2019 |
| EP | 2355762 B1 | 9/2019 |
| EP | 2822613 B1 | 9/2019 |
| EP | 2863855 B1 | 9/2019 |
| EP | 2482912 B1 | 10/2019 |
| EP | 3038667 B1 | 10/2019 |
| EP | 3129095 B1 | 10/2019 |
| EP | 3191150 B1 | 10/2019 |
| EP | 3280466 B1 | 10/2019 |
| EP | 2244756 B1 | 12/2019 |
| EP | 2968702 B1 | 12/2019 |
| FR | 2 939 320 | 6/2010 |
| GB | 2511523 | 9/2014 |
| JP | H04-354722 | 12/1992 |
| RU | 131622 | 8/2013 |
| WO | WO 2009/098696 | 8/2009 |
| WO | WO 2009/120951 | 10/2009 |
| WO | WO 2011/049562 | 4/2011 |
| WO | WO 2011/130570 | 10/2011 |
| WO | WO 2011/135285 | 11/2011 |
| WO | WO 2011/146532 | 11/2011 |
| WO | WO 2013/136181 | 9/2013 |
| WO | WO 2014/099709 | 6/2014 |
| WO | WO 2016/103031 | 6/2016 |
| WO | WO 2016/126560 | 8/2016 |
| WO | WO 2016/182977 | 11/2016 |
| WO | WO 2017/079174 | 5/2017 |
| WO | WO 2017/196888 | 11/2017 |
| WO | WO 2018/056060 | 3/2018 |
| WO | WO 2018/060412 | 4/2018 |
| WO | WO 2018/060417 | 4/2018 |
| WO | WO 2018/115461 | 6/2018 |
| WO | WO 2018/156730 | 8/2018 |
| WO | WO 2018/162613 | 9/2018 |
| WO | WO 2018/164803 | 9/2018 |
| WO | WO-2018158250 A1 | 9/2018 |
| WO | WO 2018/185138 | 10/2018 |
| WO | WO 2018/187394 | 10/2018 |
| WO | WO 2018/192978 | 10/2018 |
| WO | WO 2018/206420 | 11/2018 |
| WO | WO-2019053101 A1 | 3/2019 |
| WO | WO-2019053106 A1 | 3/2019 |
| WO | WO-2019086332 A1 | 5/2019 |
| WO | WO-2019086341 A1 | 5/2019 |
| WO | WO-2019086475 A1 | 5/2019 |
| WO | WO-2019193141 A1 | 10/2019 |

OTHER PUBLICATIONS

International Preliminary Report on Patentability for Application No. PCT/EP2018/061476, dated Nov. 21, 2019, 10 pages.

* cited by examiner

| A&B On/Off | State of SW1 | State of SW2 |
|---|---|---|
| On | Closed | Closed |
| Off | Open | Closed |
| Off | Closed | Open |
| Off | Open | Open |

REDUNDANT CONTROLS FOR NEGATIVE PRESSURE WOUND THERAPY SYSTEMS

CROSS-REFERENCE TO RELATED APPLICATIONS

This application is a national stage application under 35 U.S.C. § 371 of International Application No. PCT/EP2018/061476, filed on May 4, 2018, which claims the benefit of U.S. Provisional Application No. 62/503,697, filed May 9, 2017; the disclosures of which are hereby incorporated by reference in their entirety.

BACKGROUND

Embodiments of the present disclosure relate to methods and apparatuses for dressing and treating a wound with negative or reduced pressure therapy or topical negative pressure (TNP) therapy. In particular, but without limitation, embodiments disclosed herein relate to negative pressure therapy devices, methods for controlling the operation of TNP systems, and methods of using TNP systems.

SUMMARY

In some embodiments, an apparatus for applying negative pressure to a wound is disclosed. The apparatus can include: a negative pressure source configured to provide negative pressure to a wound dressing via a fluid flow path; a switch including an actuator configured to toggle a state of a first pair of electrical contacts and a state of a second pair of electrical contacts in response to a user input; and control circuitry configured to: supply negative pressure with the negative pressure source in response to the first pair of electrical contacts being in an electrically connected state and the second pair of electrical contacts being in the electrically connected state, and disable supply of negative pressure with the negative pressure source in response to the first pair of electrical contacts being in an electrically disconnected state or the second pair of electrical contacts being in the electrically disconnected state.

The apparatus of the preceding paragraph can include one or more of the following features: The control circuitry is configured to disable supply of negative pressure with the negative pressure source in response to the first pair of electrical contacts being in the electrically connected state and the second pair of electrical contacts being in the electrically disconnected state. The actuator is configured to simultaneously toggle the state of the first pair of electrical contacts and the state of the second pair of electrical contacts in response to the user input. The control circuitry is configured to supply negative pressure with the negative pressure source in response to no user inputs other than the user input to the switch. When the actuator is broken and no longer able to toggle the state of the first pair of electrical contacts or the state of the second pair of electrical contacts, the control circuitry is further configured to no longer supply negative pressure with the negative pressure source. The control circuitry is further configured to detect a switch fault in response to the state of the first pair of electrical contacts not toggling within a threshold period of time subsequent to toggling of the state of the second pair of electrical contacts. The threshold period of time is 0.5 seconds, 1 second, 2 seconds, 3 second, or 5 seconds. The control circuitry is further configured to output a switch fault indication in response to detection of the switch fault. The first pair of electrical contacts includes a plurality of first traces and the second pair of electrical contacts includes a plurality of second traces, and the actuator is configured to short the plurality of first traces to one another and short the plurality of second traces to one another in response to the user input. The negative pressure source is disposed on or within the wound dressing. The control circuitry is configured to disable supply of negative pressure with the negative pressure source by deactivation of operation of the negative pressure source, opening of a vent positioned in the fluid flow path, or closing of a valve positioned in the fluid flow path. The switch is configured to receive the user input as a depression of the switch.

In some embodiments, a method for controlling application of negative pressure to a wound is disclosed. The method includes: using an actuator of a switch, toggling a state of a first pair of contacts and a state of a second pair of contacts in response to receipt of a user input to the switch; supplying negative pressure with a negative pressure source to a wound dressing via a fluid flow path in response to the state of the first pair of contacts being a first state and the state of the second pair of contacts being a second state; and disabling supply of negative pressure with the negative pressure source in response to the state of the first pair of contacts not being the first state or the state of the second pair of contacts not being the second state, wherein the state of the first pair of contacts is the first state and the state of the second pair of contacts is the second state at a first time, and the state of the first pair of contacts is not the first state and the state of the second pair of contacts is not the second state at a second time.

The method of the preceding paragraph can include one or more of the following features: The first and second states correspond to forming an electrical connection. At a third time, the state of the first pair of contacts is the first state and the state of the second pair of contacts is not the second state. The toggling includes simultaneously toggling the state of the first pair of contacts and the state of the second pair of contacts in response to receipt of the user input to the switch. The method further includes detecting a switch fault in response to the state of the first pair of contacts not toggling within a threshold period of time subsequent to toggling of the state of the second pair of contacts. The threshold period of time is between 0.5 seconds and 5 seconds. The method further includes outputting a switch fault indication for presentation to a user in response to the detecting. The disabling includes disabling supply of negative pressure with the negative pressure source by deactivation of operation of the negative pressure source, opening of a vent positioned in the fluid flow path, or closing of a valve positioned in the fluid flow path.

BRIEF DESCRIPTION OF THE DRAWINGS

Features and advantages of the present disclosure will be apparent from the following detailed description, taken in conjunction with the accompanying drawings of which.

DETAILED DESCRIPTION

Figure 1:
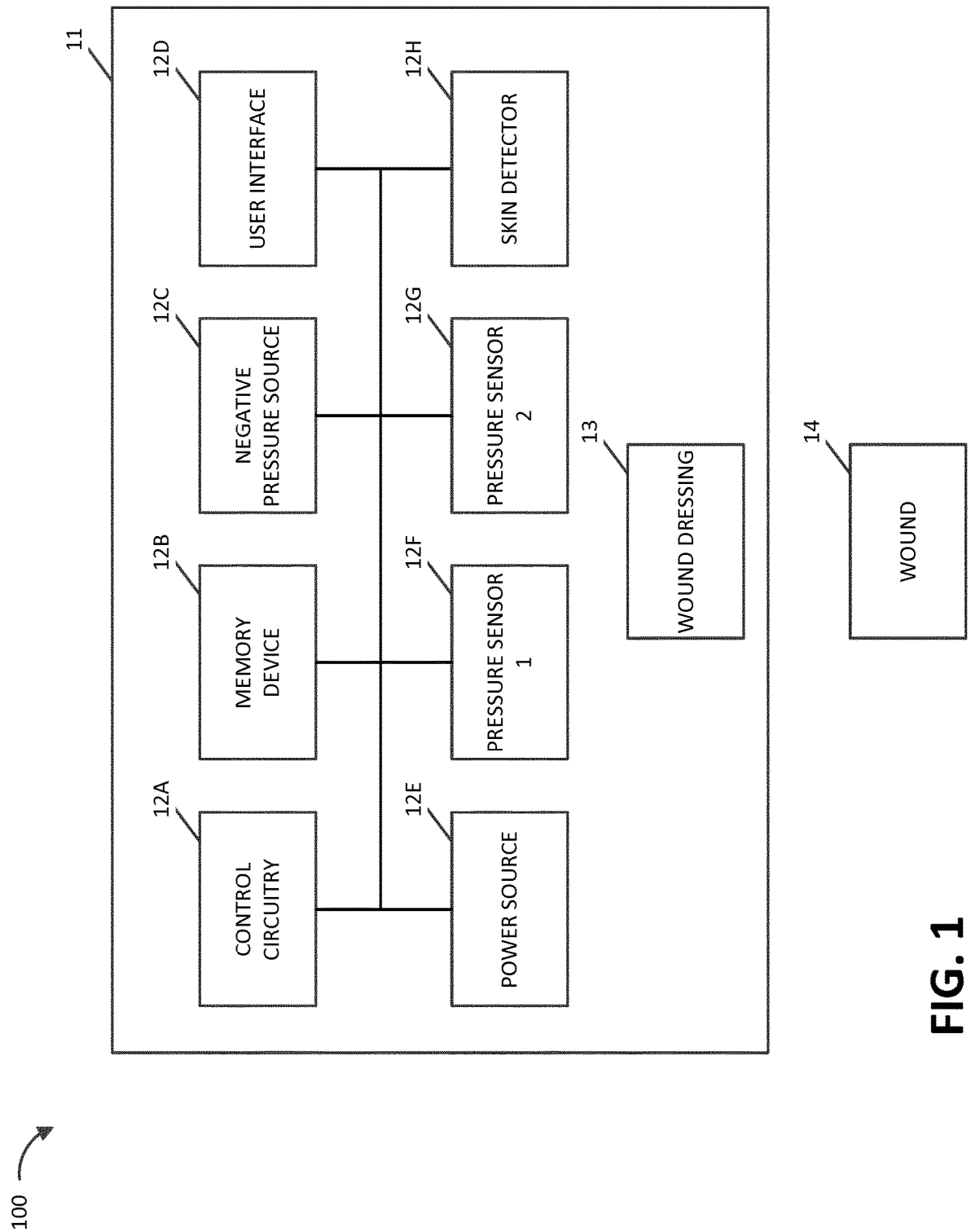
FIG. 1 illustrates a negative pressure therapy system according to some embodiments.

The present disclosure relates to methods and apparatuses for dressing and treating a wound with reduced pressure therapy or topical negative pressure (TNP) therapy. In particular, but without limitation, embodiments of this disclosure relate to negative pressure therapy apparatuses, methods for controlling the operation of TNP systems, and methods of using TNP systems. The methods and apparatuses can incorporate or implement any combination of the features described below. In certain embodiments, the features of this disclosure can advantageously increase the safety of a patient when using a TNP apparatus.

Many different types of wound dressings are known for aiding in the healing process of a human or animal. These different types of wound dressings include many different types of materials and layers, for example, gauze, pads, foam pads or multi-layer wound dressings. TNP therapy, sometimes referred to as vacuum assisted closure, negative pressure wound therapy, or reduced pressure wound therapy, can be a beneficial mechanism for improving the healing rate of a wound. Such therapy is applicable to a broad range of wounds such as incisional wounds, open wounds and abdominal wounds or the like.

TNP therapy can assist in the closure and healing of wounds by reducing tissue oedema, encouraging blood flow, stimulating the formation of granulation tissue, removing excess exudates, and reducing bacterial load and thus, infection to the wound. Furthermore, TNP therapy can permit less outside disturbance of the wound and promote more rapid healing.

As is used herein, reduced or negative pressure levels, such as −X mmHg, represent pressure levels that are below atmospheric pressure, which typically corresponds to 760 mmHg (or 1 atm, 29.93 inHg, 101.325 kPa, 14.696 psi, etc.). Accordingly, a negative pressure value of −X mmHg reflects pressure that is X mmHg below atmospheric pressure, such as a pressure of (760−X) mmHg. In addition, negative pressure that is "less" or "smaller" than −X mmHg corresponds to pressure that is closer to atmospheric pressure (e.g., −40 mmHg is less than −60 mmHg). Negative pressure that is "more" or "greater" than −X mmHg corresponds to pressure that is further from atmospheric pressure (e.g., −80 mmHg is more than −60 mmHg).

Overview

The user interfaces of some TNP apparatuses may have a limited elements through which a user can provide user input. In some instances, particular user interfaces may include just a single element usable by the user to stop and start operation of the TNP apparatus, such as the delivery of negative pressure, and the user may not be able to replace or interchange the functionality of the single element with that of another element. These particular user interfaces can desirably be easier to construct and operate than more complicated user interfaces having numerous elements. However, the particular user interfaces may present a problem if the single element experiences a fault (for example, a failure) and is no longer able to function as expected. The user of the particular user interfaces may, for example, undesirably be unable to pause or stop delivery of negative pressure if negative pressure is being provided by the TNP apparatus.

The situation of a user being unable to stop delivery of negative pressure can additionally introduce risks to the healing of a wound of a patient or to the patient's health. If the patient experiences discomfort from the wound dressing during delivery of negative pressure and the single element fails such that it is no longer able to function to receive user input, the patient may be forced to either continue application of negative pressure therapy despite the dangers or remove the wound dressing, cut or sever one of the tubes or lumens (which may not be possible when a source of negative pressure is integrated in a wound dressing), break the TNP apparatus (for example, by pulling out electronics if possible), remove the power source (if accessible), or the like to terminate delivery of negative pressure. These actions (for example, removal of the wound dressing) can damage the wound of the patient and hinder any healing trajectory that was already progressed, as well as expose the wound to external contaminants due to a loss of protection from the wound dressing.

To help prevent the situation of the user being unable to stop delivery of negative pressure when it is necessary to do so, a TNP apparatus with the single element usable by the user to stop and start delivery of negative pressure can include redundant activation or deactivation controls or mechanisms within the single element. In one example, the single element can be a switch that includes an actuator configured to toggle a state of a first pair of contacts and a state of a second pair of contacts. If the state of either or both of the first or second pair of contacts is toggled during delivery of negative pressure therapy, the TNP apparatus is caused to disable delivery of negative pressure therapy. Accordingly, in the event that the actuator may be broken and only able to toggle the state of one of the first and second pair of contacts, the actuator may nonetheless be usable to stop delivery of negative pressure with the TNP apparatus.

Reduced Pressure Therapy Systems and Methods

FIG. 1 illustrates a negative pressure therapy system 100 that includes a TNP apparatus 11 and a wound 14. The TNP apparatus 11 can be used to treat the wound 14. The TNP apparatus 11 can include control circuitry 12A, memory 12B, a negative pressure source 12C, a user interface 12D, a power source 12E, a first pressure sensor 12F, a second pressure sensor 12G (which may be optional), and a skin detector 12H that are configured to electrically communicate with one another. In addition, the TNP apparatus 11 can include a wound dressing 13. The power source 12E can provide power to one or more components of the TNP apparatus 11.

One or more of the control circuitry 12A, memory device 12B, negative pressure source 12C, user interface 12D, power source 12E, first pressure sensor 12F, second pressure sensor 12G, and skin detector 12H can be integral with, incorporated as part of, attached to, or disposed in the wound dressing 13. The TNP apparatus 11 can accordingly be considered to have its control electronics and pump on-board the wound dressing 13 rather than separate from the wound dressing 13.

The control circuitry 12A can include one or more controllers, activation circuits, boost converters, current limiters, feedback conditioning circuits, and H-bridge inverters. The one or more controllers can control the operations of one or more other components of the TNP apparatus 11 according at least to instructions stored in the memory device 12B. The one or more controllers can, for instance, control operations of the negative pressure source 12C via a signal input (for example, a pulse width modulation of the signal) to the one or more H-bridge inverters, which in turn drive power from the power source 12E to the negative pressure source 12C.

The negative pressure source 12C can include a pump, such as, without limitation, a rotary diaphragm pump or other diaphragm pump, a piezoelectric pump, a peristaltic pump, a piston pump, a rotary vane pump, a liquid ring pump, a scroll pump, a pump operated by a piezoelectric transducer, a voice coil pump, or any other suitable pump or micropump or any combinations of the foregoing.

The user interface 12D can include one or more elements that receive user inputs or provide user outputs to a patient or caregiver. The one or more elements that receive user inputs can include buttons, switches, dials, touch screens, or the like, and the one or more elements that provide user outputs can include activation of a light emitting diode (LED) or one or more pixels of the display or activation of a speaker or the like. In one example, the user interface 12D can include a switch to receive a first user input (for instance, a negative pressure activation or deactivation input) and two LEDs to indicate an operating status (for example, functioning normally, under fault condition, or awaiting user input) of the TNP apparatus 11.

The first pressure sensor 12F can be used to monitor pressure underneath the wound dressing 13, such as pressure in a fluid flow path connecting the negative pressure source 12C and the wound 14, pressure at the wound 14, or pressure in the negative pressure source 12C. The second pressure sensor 12G can be used to monitor pressure external to the wound dressing 13. The pressure external to the wound dressing can be atmospheric pressure; however, the atmospheric pressure can vary depending on, for instance, an altitude of use or pressurized environment in which the TNP apparatus 11 may be used.

The control circuitry 12A can control the supply of negative pressure by the negative pressure source 12C according at least to a comparison between the pressure monitored by the first pressure sensor 12F and the pressure monitored by the second pressure sensor 12G. The control circuitry 12A can include a controller, such as a microcontroller or microprocessor.

The skin detector 12H can be used to determine if the wound dressing 13 has been placed over the wound 14. The skin detector 12H can, for example, detect skin of a patient. The detection by the skin detector 12H can confirm whether the wound dressing 13 is coupled to skin of the patient next to the wound 14. When skin is detected, this may indicate that activation of the TNP apparatus 11 is intentional rather than unintentional and can thus be used to prevent unintentional activation of the TNP apparatus 11 or an end-of-life timer of the TNP apparatus 11, such as during transportation or manufacture of the TNP apparatus 11. In one example, if the skin detector 12H indicates to the control circuitry 12A that skin is detected, the control circuitry 12A can activate the negative pressure source 12C to supply negative pressure in response to receiving an activation input via the user interface 12D. If the skin detector 12H, on the other hand, indicates to the control circuitry 12A that skin is not detected, the control circuitry 12A may not activate the negative pressure source 12C to supply negative pressure in response to receiving an activation input via the user interface 12D. The skin detector 12H can include one or more of a capacitive sensor, an impedance sensor, an optical sensor, a piezoresistive sensor, a piezoelectric sensor, an elastoresistive sensor, and an electrochemical sensor.

The wound dressing 13 can include a wound contact layer, a spacer layer, and an absorbent layer. The wound contact layer can be in contact with the wound 14. The wound contact layer can include an adhesive on the patient facing side for securing the dressing to the skin surrounding the wound 14 or on the top side for securing the wound contact layer to a cover layer or other layer of the wound dressing 13. In operation, the wound contact layer can provide unidirectional flow so as to facilitate removal of exudate from the wound while blocking or substantially preventing exudate from returning to the wound 14. The spacer layer can assist in distributing negative pressure over the wound site and facilitating transport of wound exudate and fluids into the wound dressing 13. Further, the absorbent layer can absorb and retain exudate aspirated from the wound 14.

The control circuitry 12A can, in some instances, prevent supply of negative pressure with the negative pressure source 12C. For example, the control circuitry 12A can prevent supply of negative pressure by deactivating operation of the negative pressure source, opening a vent positioned in the fluid flow path, and closing a valve positioned in the fluid flow path.

The supply of negative pressure with the negative pressure source 12C can, in some instances, be disabled. For example, supply of negative pressure can be disabled by deactivating operation of the negative pressure source 12C or the control circuitry 12A, opening a vent positioned in the fluid flow path, and closing a valve positioned in the fluid flow path. In some implementations, deactivating operation of the negative pressure source 12C or the control circuitry 12A can be performed by disconnection of power to the negative pressure source 12C or the control circuitry 12A or withdrawal of an enable signal provided to the negative pressure source 12C or the control circuitry 12A.

The control circuitry 12A can monitor a duty cycle of the negative pressure source 12C. As is used herein, the "duty cycle" can reflect the amount of time the negative pressure source 12C is active or running over a period of time. In other words, the duty cycle can reflect time that the negative pressure source 12C is in an active state as a fraction of total time under consideration. Duty cycle measurements can reflect a level of activity of the negative pressure source 12C. For example, the duty cycle can indicate that the negative pressure source 12C is operating normally, working hard, working extremely hard, etc. Moreover, the duty cycle measurements, such as periodic duty cycle measurements, can reflect various operating conditions, such as presence or severity of leaks, rate of flow of fluid (for instance, air, liquid, or solid exudate, etc.) aspirated from a wound, or the like. Based on the duty cycle measurements, such as by comparing the measured duty cycle with a set of thresholds (for instance, determined in calibration), the controller can execute or be programmed to execute algorithms or logic that control the operation of the system. For example, duty cycle measurements can indicate presence of a high leak, and the control circuitry 12A can be programmed to indicate this condition to a user (for instance, patient, caregiver, or physician) or temporarily suspend or pause operation of the source of negative pressure in order to conserve power.

When the TNP apparatus 11 may be used to treat the wound 14, the wound dressing 13 can create a substantially sealed or closed space around the wound 13 and under the wound dressing 13, and the first pressure sensor 12F can periodically or continuously measure or monitor a level of pressure in this space. The control circuitry 12A can control the level of pressure in the space between a first negative pressure set point limit and at least a second negative pressure set point limit. In some instances, the first set point limit can be approximately −70 mmHg, or from approximately −60 mmHg or less to approximately −80 mmHg or more. In some instances, the second set point limit can be approximately −90 mmHg, or from approximately −80 mmHg or less to approximately −100 mmHg or more.

Figure 2A:
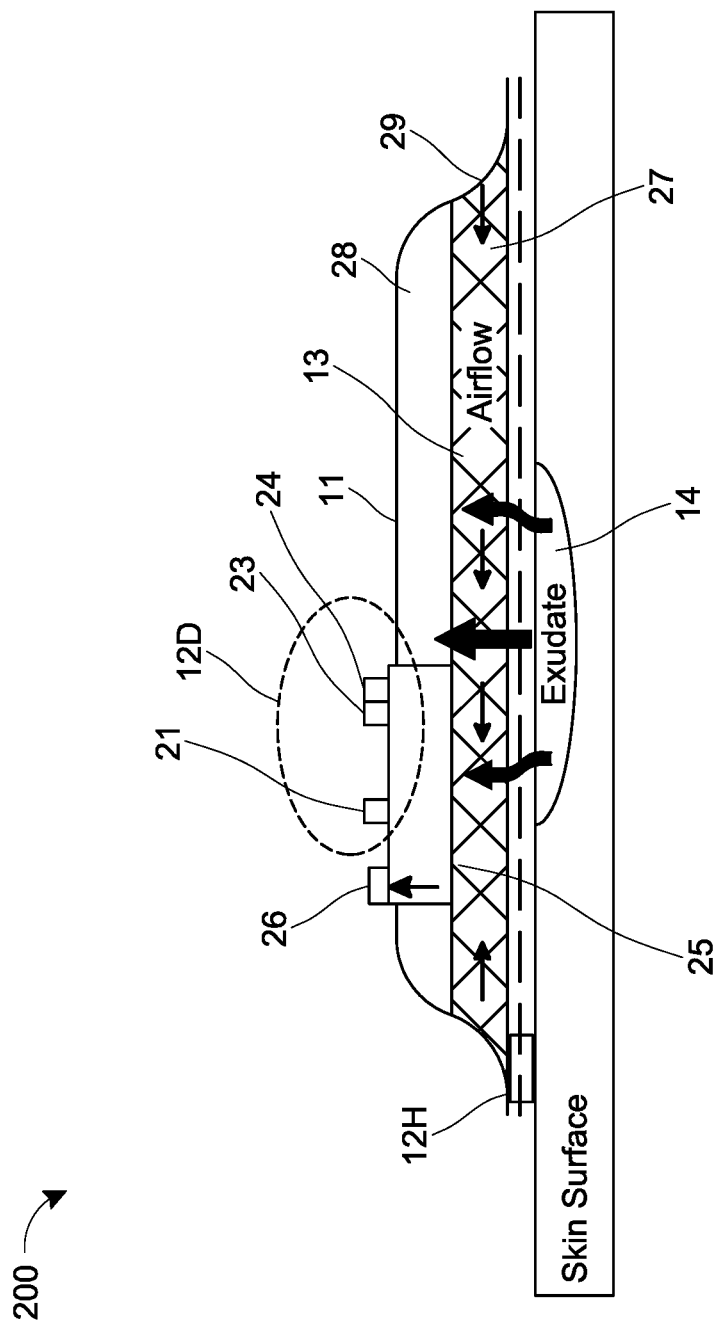
FIGS. 2A and 2B respectively illustrate a side view and top view of a negative pressure therapy system, such as the negative pressure therapy system of FIG. 1, according to some embodiments.
Figure 2B:
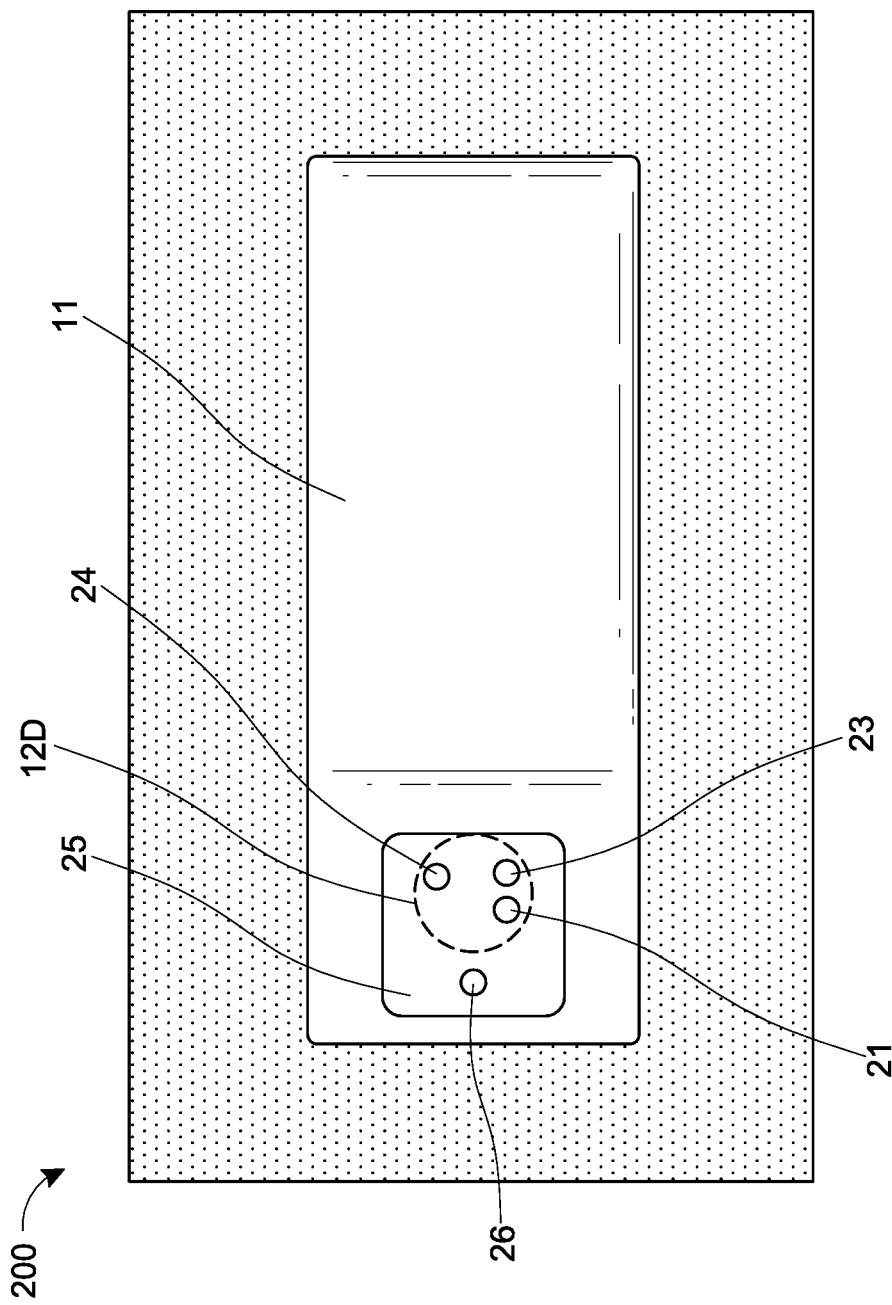

FIG. 2A illustrates a side view of a negative pressure therapy system 200, and FIG. 2B illustrates a top view of the negative pressure therapy system 200. The negative pressure therapy system 200 can be an example implementation of the negative pressure therapy system 100.

In the negative pressure therapy system 200, the wound dressing 13 of the TNP apparatus 11 is shown as attached to the wound 14. Arrows depict the flow of air through the wound dressing 13 and wound exudate from the wound 14. The TNP apparatus 11 can include an air exhaust 26 and a component area 25, such as a components housing or storage area for components of the TNP apparatus 11 like one or more of the control circuitry 12A, memory device 12B, negative pressure source 12C, user interface 12D, power source 12E, first pressure sensor 12F, second pressure sensor 12G, and skin detector 12H.

The user interface 12D of the negative pressure therapy system 200 can include a switch 21, a first indicator 23 (such as a first LED), and a second indicator 24 (such as a second LED). The switch 21 can receive a negative pressure activation or deactivation user input (for example, such as receiving the activation or deactivation user input in response to depression of the switch 21). The first indicator 23 and the second indicator 24 can indicate an operating status like functioning normally, under fault condition, or awaiting user input. In some implementations, the switch 21 can couple to a power supply connection of the negative pressure source 12C or the control circuitry 12A (such as a controller of the control circuitry 12A) or an enable signal of the negative pressure source 12C or the control circuitry 12A to activate or deactivate supply of negative pressure or disable supply of negative pressure. Moreover, the control circuitry 12A can monitor the user interface 12D, such as the switch 21, the first indicator 23, or the second indicator 24, to detect issues like a fault and, responsive to the fault detection, output a fault indication via the user interface 12D or activate or deactivate supply of negative pressure or disable supply of negative pressure. In certain embodiments, the control circuitry 12A may supply negative pressure with the negative pressure source 12C in response to no user inputs other a user input to the switch 21.

Component parts of the wound dressing 13 of the negative pressure therapy system 200 are illustrated to include an airlock layer 27, an absorbing layer 28, and a contact layer 29. The airlock layer 27 can enable air flow. The absorbing layer 28 can absorb wound exudate. The contact layer 29 can be soft and include silicon and be used to couple the TNP apparatus 11 to the patient.

Figures 3A, 3B:
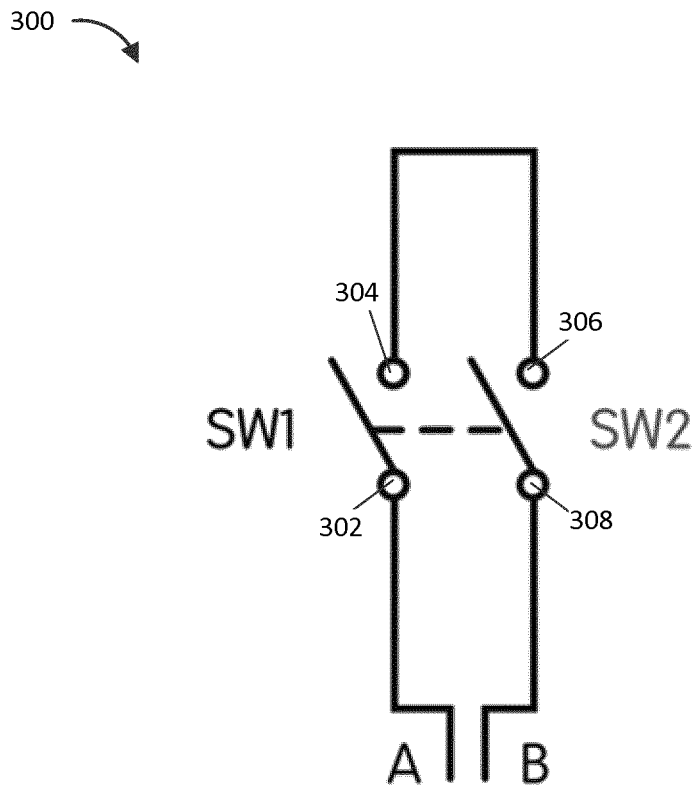
FIG. 3A illustrates a circuit schematic for a switch of a negative pressure therapy system, such as the negative pressure therapy system of FIG. 1, according to some embodiments.
FIG. 3B is a logical truth table for the circuit schematic of FIG. 3A according to some embodiments.

FIG. 3A illustrates a circuit schematic 300 for a switch like the switch 21, according to some embodiments. The switch can be a double pole, single throw switch and include an actuator that toggles states of multiple sets of contacts (for example, two, three, four, or more sets of contacts) in response to a user input, such as a depression of the switch. The actuator can simultaneously or in a staggered manner toggle the states of the multiple sets of contacts. As illustrated in FIG. 3A, the multiple sets of contacts include a first pair of contacts including contacts 302 and 304 (collectively with a first contact pad forming a first switch, which can be referred to as SW1) and a second pair of contacts including contacts 306 and 308 (collectively with a first contact pad forming a second switch, which can be referred to as SW2). SW1 and SW2 can act as redundant switches. Although the schematic 300 illustrates two pairs of contacts, any of the switches described herein can include more than two pairs of contacts.

The contacts 302 and 304 are shown as open, and the contacts 306 and 308 are shown as open. The contacts 302 and 304 may be open because a contact pad of SW1 is not electrically connecting or shorting the contacts 302 and 304 together. When the contacts 302 and 304 are open, SW1 may also be considered to be open. Similarly, the contacts 306 and 308 may be open because a contact pad of SW2 is not electrically connecting or shorting the contacts 306 and 308 together. When the contacts 306 and 308 are open, SW2 may also be considered to be open.

The contacts 302 and 304 may be closed when the contact pad of SW1 electrically connects or shorts the contacts 302 and 304 together. When the contacts 302 and 304 are closed, SW1 may also be considered to be closed. The contacts 306 and 308 may be closed when the contact pad of SW2 electrically connects or shorts the contacts 306 and 308 together. When the contacts 306 and 308 are closed, SW2 may also be considered to be closed.

The switch can further include an input A and an output B. For example, the input A can be electrically coupled to either power (for example, the power source 12E) or ground of the TNP apparatus 11, and the output B can be electrically coupled to control operations of the TNP apparatus (or vice versa). When the switch is closed, an electrical connection to power or ground is formed thereby enabling the TNP apparatus 11 to operate or function to provide therapy. For instance, when the switch is closed, a signal may be provided or generated to the control circuitry 12A to activate the negative pressure source 12C or enable supply of power by the power source 12E to other components of the TNP apparatus 11.

In some implementations, when the switch is functioning properly, the states of the multiple sets of contacts may toggle only in response to the user input to switch. If switch is broken, however, and the actuator is no longer able to toggle one or more of the multiple sets of contacts, the switch may no longer toggle states of all of the multiple sets of contacts in response to the user input. Accordingly, if the actuator is no longer able to toggle one or more of the multiple sets of contacts, the control circuitry 12A may no longer be configured to supply negative pressure with the negative pressure source 12C.

FIG. 3B is a logical truth table 310 for the circuit schematic 300. As can be understood from the logical truth table 310, the electrical path from the input A to the output B can be considered to be formed or "on" if both SW1 and SW2 are closed, and the electrical path from the input A to the output B can be considered to be not formed or "off" if at least one of SW1 or SW2 is open.

In other implementations, a switch can be designed differently from the circuit schematic 300 and be made to function according to an alternative logical truth table different from the logical truth table 310. The alternative logical truth table can include multiple possible configurations and each configuration cause the electrical path from the input A to the output B to be either on or off. One or more of the multiple possible configurations of the alternative logical truth table can cause the electrical path from the input A to the output B to be on, and the one or more other of the multiple configurations of the alternative logical truth table can cause the electrical path from the input A to the output B being off. In certain embodiments, a total number of the multiple configurations which cause the electrical path from the input A to the output B to be on can be less than a total number of the multiple configurations which cause the electrical path from the input A to the output B to be off. This may advantageously result in a bias toward causing the electrical path from the input A to the output B to be off unless the switch is properly functioning. As a result, the switch may intelligently cause the negative pressure source 12C to operate when the switch is properly functioning but not when the switch is not properly functioning.

Figure 4B:
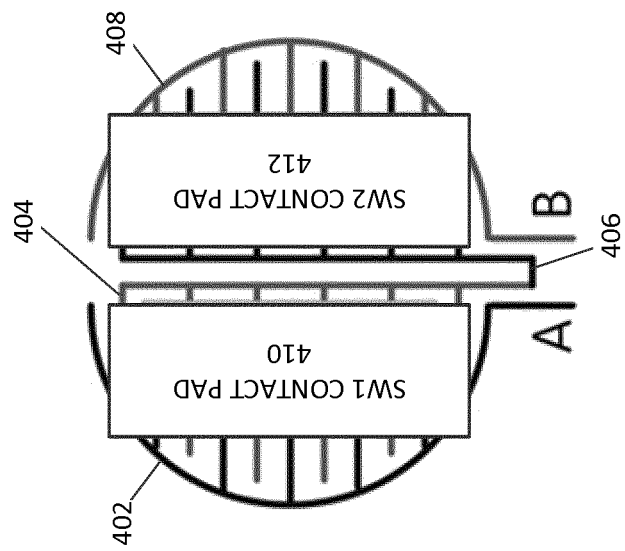
FIGS. 4A, 4B, 5A, 5B, 6A, and 6B illustrate implementations of the circuit schematic of FIG. 3A according to some embodiments.
Figure 4A:
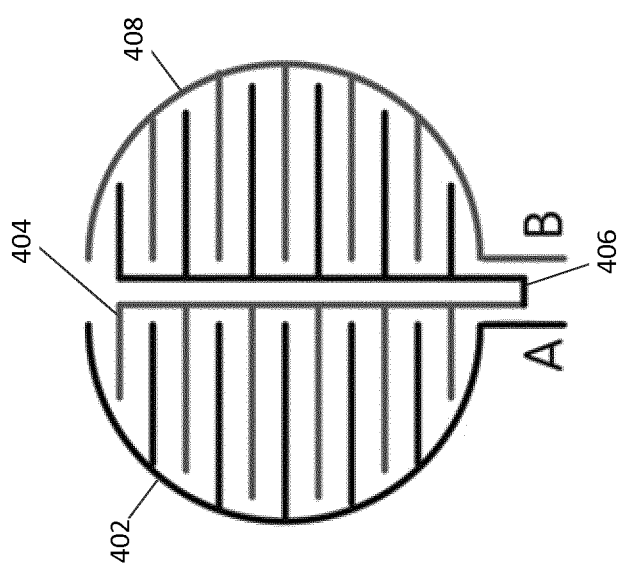

FIGS. 4A and 4B illustrate an implementation of the circuit schematic 300, according to some embodiments. Contacts 402, 404, 406, 408 can respectively be implementations of the contacts 302, 304, 306, 308. The SW1 contact pad 410 can be an implementation of the contact pad of SW1 of FIG. 3A, and the SW2 contact pad 412 can be an implementation of the contact pad of SW2 of FIG. 3A.

As illustrated, at least some of the contacts 402, 404, 406, 408 can each include a primary trace and multiple secondary traces extending from the primary trace. The multiple secondary traces can each extend perpendicular to the primary trace from which it extends. The primary traces can be curved as shown with respect to the contacts 402 and 408 or straight as shown with respect to the contacts 404 and 406. The primary and secondary traces of the contacts 402, 404, 406, 408 can be printed, for example, on a circuit board.

In FIG. 4A, the contacts 402 and 404 are shown as open, and the contacts 406 and 408 are shown as open. In FIG. 4B, the contacts 402 and 404 are shown as closed due to contact of the SW1 contact pad 410 with the contacts 402 and 404, and the contacts 406 and 408 are shown as closed due to contact of the SW2 contact pad 412 with the contacts 406 and 408. An electrical path is formed from the input A to the output B, for example, through the contact 402, contact pad 410, contact 404, contact 406, contact pad 412, and contact 408. The SW1 contact pad 410 and the SW2 contact pad 412 can be conductive plates. Contact pads 410 and 412 may be brought into contact with the contacts 402, 404, 406, 408 by an actuator (or actuators), which can be mechanically, pneumatically, electrically, or the like actuated by a user input, such as a depression of the switch.

Figure 5B:
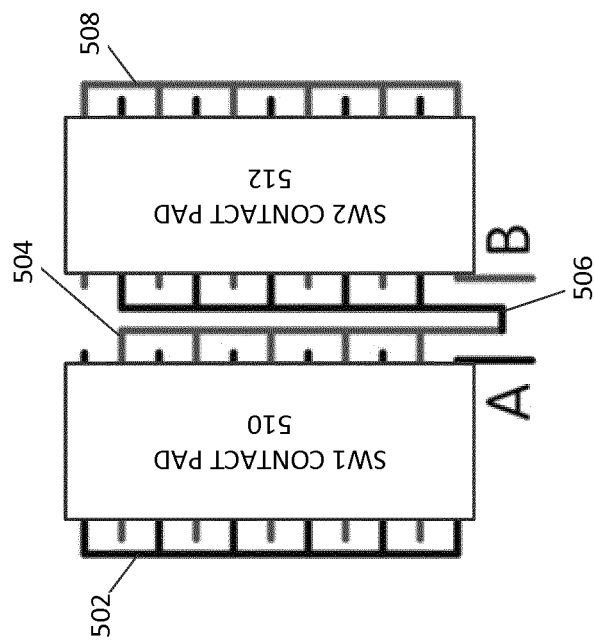
Figure 5A:
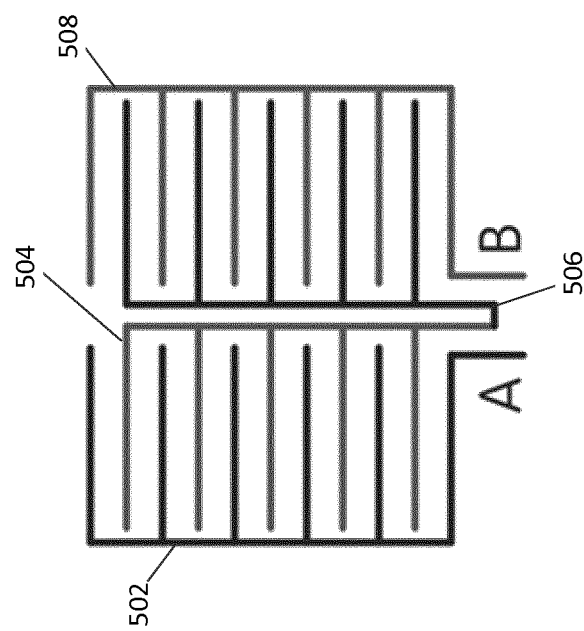

FIGS. 5A and 5B illustrate another implementation of the circuit schematic 300, according to some embodiments. Contacts 502, 504, 506, 508 can respectively be implementations of the contacts 302, 304, 306, 308. The SW1 contact pad 510 can be an implementation of the contact pad of SW1 of FIG. 3A, and the SW2 contact pad 512 can be an implementation of the contact pad of SW2 of FIG. 3A.

As illustrated, at least some of the contacts 502, 504, 506, 508 can each include a primary trace and multiple secondary traces extending from the primary trace. The multiple secondary traces can each extend perpendicular to the primary trace from which it extends. The primary traces can be straight as shown. The primary and secondary traces of the contacts 502, 504, 506, 508 can be printed, for example, on a circuit board.

In FIG. 5A, the contacts 502 and 504 are shown as open, and the contacts 506 and 508 are shown as open. In FIG. 5B, the contacts 502 and 504 are shown as closed due to contact of the SW1 contact pad 510 with the contacts 502 and 504, and the contacts 506 and 508 are shown as closed due to contact of the SW2 contact pad 512 with the contacts 506 and 508. An electrical path is formed from the input A to the output B, for example, through the contact 502, contact pad 510, contact 504, contact 506, contact pad 512, and contact 508. The SW1 contact pad 510 and the SW2 contact pad 512 can be conductive plates. Contact pads 510 and 512 may be brought into contact with the contacts 502, 504, 506, 508 by an actuator (or actuators), which can be mechanically, pneumatically, electrically, or the like actuated by a user input like a depression of the switch.

Figure 6B:
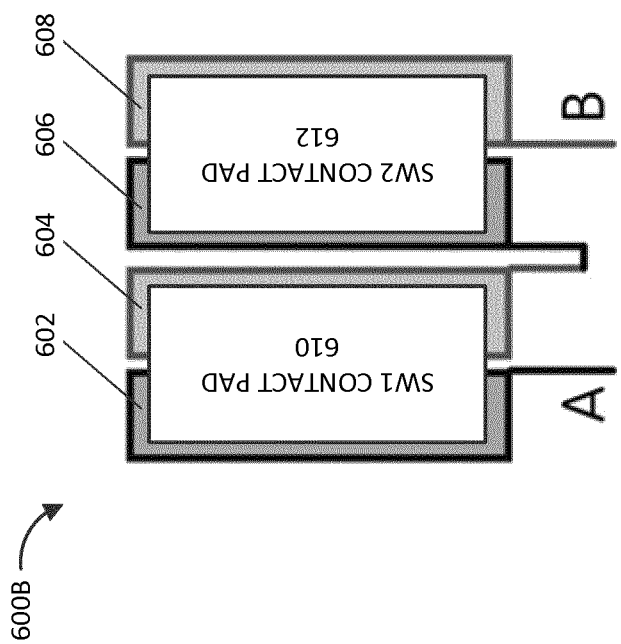
Figure 6A:
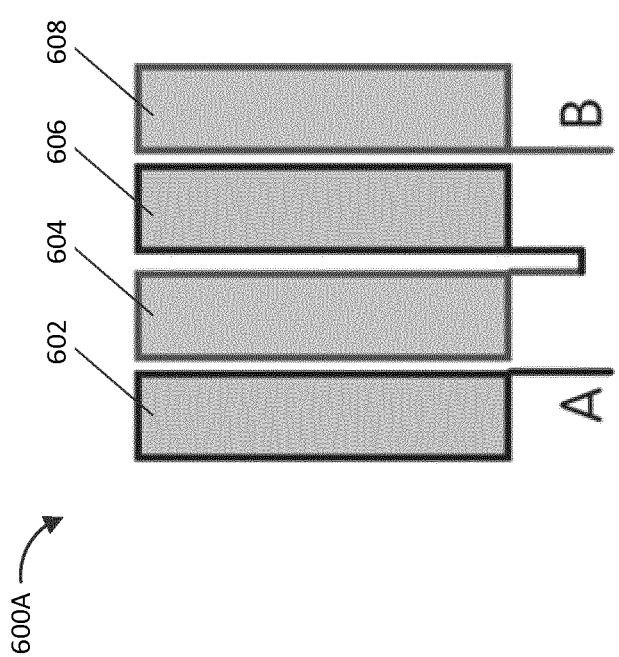

FIGS. 6A and 6B illustrate another implementation of the circuit schematic 300, according to some embodiments. Contacts 502, 604, 606, 608 can respectively be implementations of the contacts 302, 304, 306, 308. The SW1 contact pad 610 can be an implementation of the contact pad of SW1 of FIG. 3A, and the SW2 contact pad 612 can be an implementation of the contact pad of SW2 of FIG. 3A.

As illustrated, at least some of the contacts 602, 604, 606, 608 can each include a perimeter trace that extends around a conductive area. The perimeter trace and the contact area of the contacts 602, 604, 606, 608 can be printed, for example, on a circuit board.

In FIG. 6A, the contacts 602 and 604 are shown as open, and the contacts 606 and 608 are shown as open. In FIG. 6B, the contacts 602 and 604 are shown as closed due to contact of the SW1 contact pad 610 with the contacts 602 and 604, and the contacts 606 and 608 are shown as closed due to contact of the SW2 contact pad 612 with the contacts 606 and 608. An electrical path is formed from the input A to the output B, for example, through the contact 602, contact pad 610, contact 604, contact 606, contact pad 612, and contact 608. The SW1 contact pad 610 and the SW2 contact pad 612 can be conductive plates. Contact pads 610 and 612 may be brought into contact with the contacts 602, 604, 606, 608 by an actuator (or actuators), which can be mechanically, pneumatically, electrically, or the like actuated by a user input like a depression of the switch.

Figure 7:
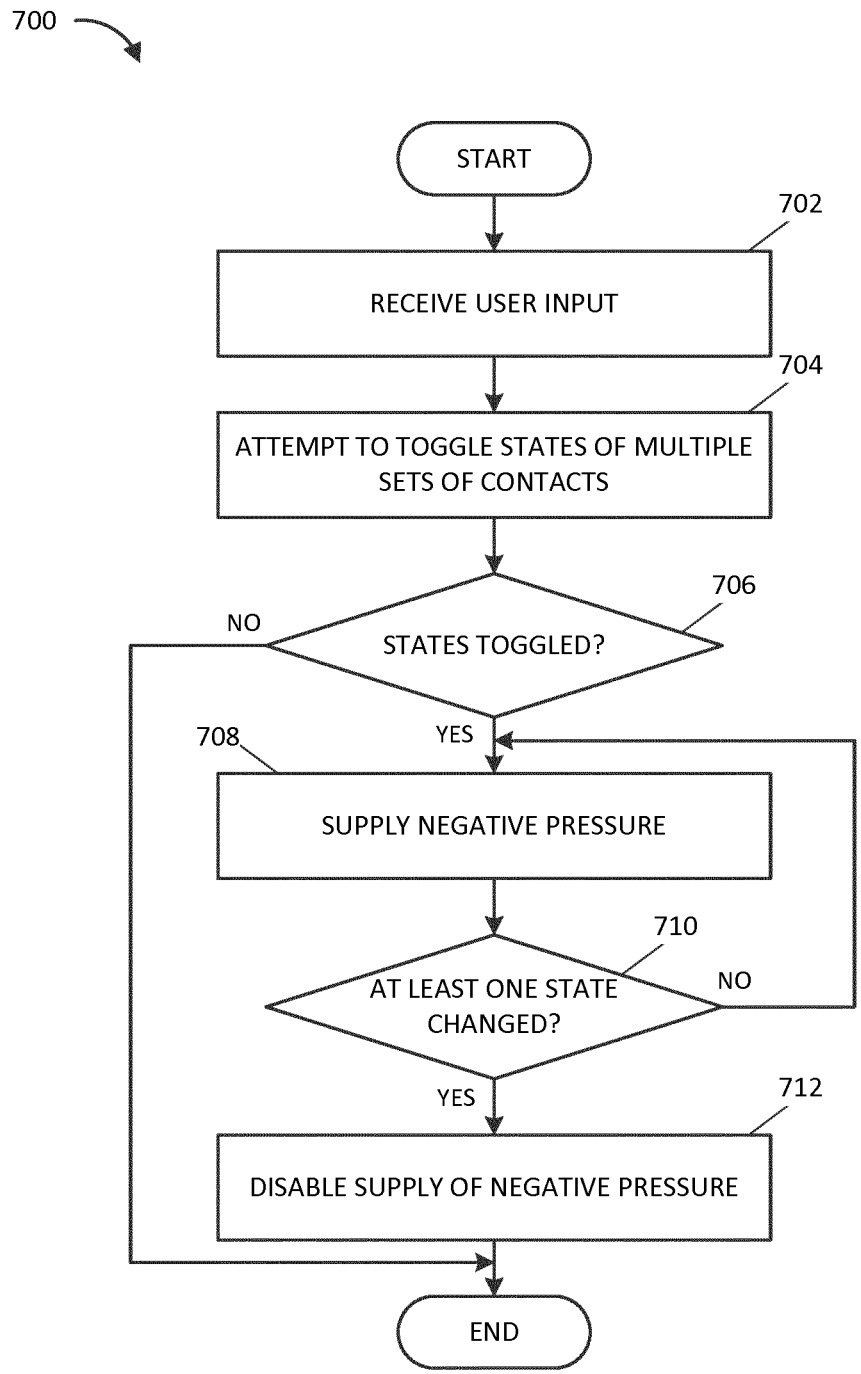
FIG. 7 illustrates a therapy control process usable to control delivery of negative pressure therapy in a negative pressure therapy system, such as the negative pressure therapy system of FIG. 1, according to some embodiments.

FIG. 7 illustrates a therapy control process 700 usable to control delivery of negative pressure therapy by an apparatus, such as the TNP apparatus 11. For convenience, the therapy control process 700 is described in the context of the TNP apparatus 11, but may instead be implemented in other systems described herein or by other systems not shown. The therapy control process 700 can be performed, in some instances, by the control circuitry 12A alone or in combination with the user interface 12D of the TNP apparatus 11.

At block 702, the therapy control process 700 can receive a user input. The user input can be received, for instance, via the user interface 12D, such as by depression of the switch 21.

At block 704, the therapy control process 700 can attempt to toggle states of multiple sets of contacts (for example, close the contacts) in response to the user input. The switch 21 can, for example, include an actuator (or actuators) that can attempt to toggle the states of multiple pairs of contacts like the contacts 302 and 304 and the contacts 306 and 308. If the switch 21 is functioning properly, the switch 21 can toggle the states of the multiple pairs of contacts. For example, the state of the multiple pairs of contacts can each be toggled simultaneously (or substantially so) or one after another so that each of the multiple pairs of contacts is closed. If the switch 21 is not functioning properly, the switch 21 may not toggle the state of one or more of the multiple pairs of contacts.

At block 706, if the states of the multiple sets of contacts were not toggled, the therapy control process 700 can end. On the other hand, if the states of the multiple sets of contacts were toggled, the therapy control process 700 can move to block 708 to supply negative pressure. The supply of negative pressure can be initiated by the control circuitry 12A and performed by the negative pressure source 12C, and the negative pressure can be supplied to the wound dressing 13 via the fluid flow path.

At block 710, if the states of the multiple sets of contacts remain unchanged, the therapy control process 700 can move again to block 708 and the supply of negative pressure can continue. On the other hand, at block 710, if the state of at least one of the multiple sets of contacts is changed (for example, opened), the therapy control process 700 can move to block 712. For example, a user input can be received via the user interface 12D, such as by depression of the switch 21, and may cause the state of one or more of the multiple pairs of contacts to toggle. If the switch 21 is functioning properly, the switch 21 can toggle the states of the multiple pairs of contacts. For example, the state of the multiple pairs of contacts can each be toggled simultaneously (or substantially so) or one after another so that each of the multiple pairs of contacts is opened. If the switch 21 is not functioning properly, the switch 21 may not toggle the state of one or more of the multiple pairs of contacts.

At block 712, the therapy control process 700 can disable supply of negative pressure. The supply of negative pressure can, for instance, be disabled by deactivation of operation of the negative pressure source 12C or the control circuitry 12A, opening of a vent positioned in the fluid flow path, and closing of a valve positioned in the fluid flow path. Because the toggling of fewer than all of the multiple sets of contacts at block 710 (for example, opening) may result in the therapy control process 700 moving from block 710 to block 712, the therapy control process 700 can advantageously, in certain embodiments, favor disabling or be biased to disable the supply of negative pressure in response to some indication to disable supply of negative pressure despite not receiving an expected indication to disable supply of negative pressure that may involve toggling of all of the multiple sets of contacts. After block 712, the therapy control process 700 can end. In some embodiments, block 710 can be performed periodically or in response to a change in the state of one or more contacts (such as, as a result of an interrupt being generated when the state of one or more contacts is toggled). In certain implementations, block 710 can be performed while negative pressure is being supplied.

Figure 8:
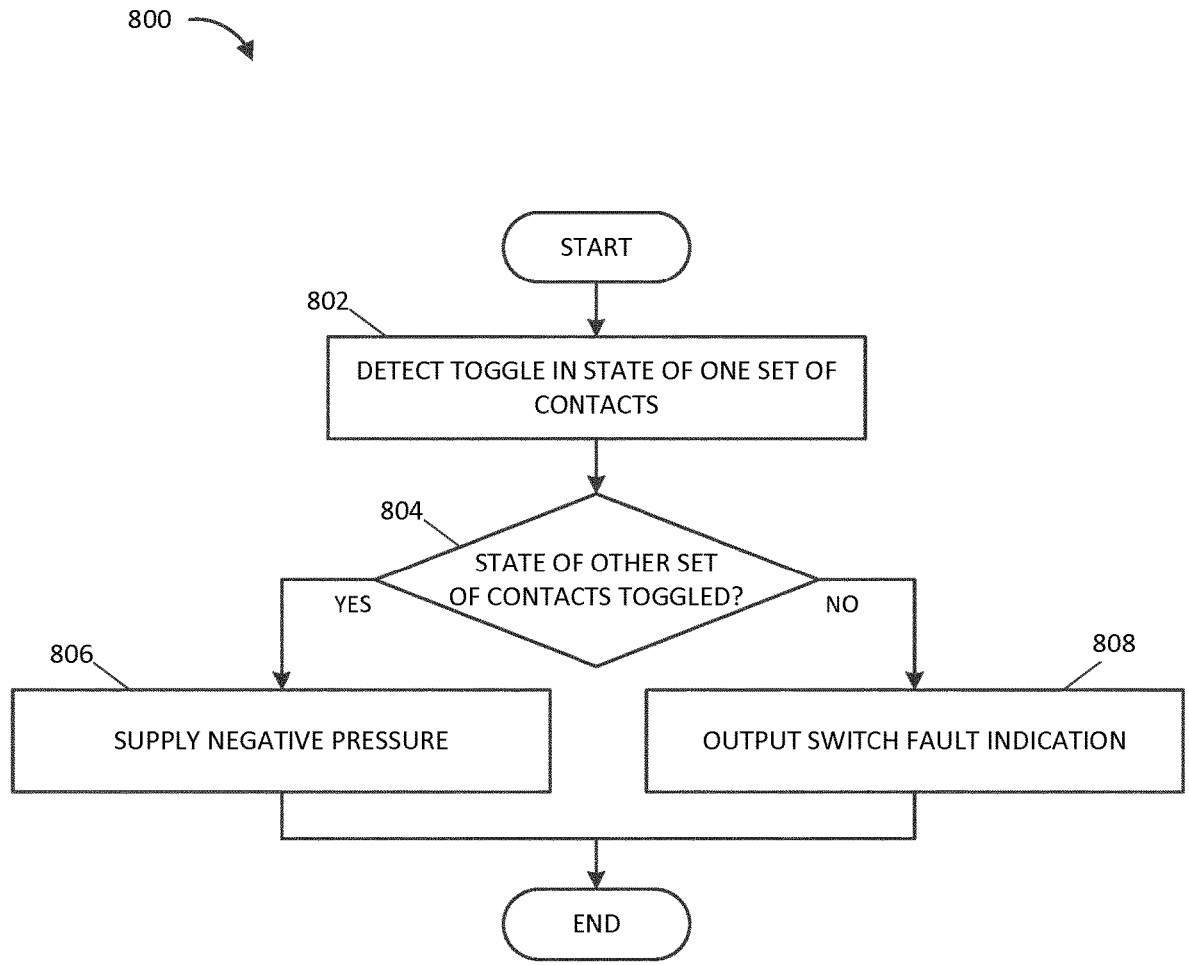
FIG. 8 illustrates a switch fault detection process usable to detect a switch fault in a negative pressure therapy system, such as the negative pressure therapy system of FIG. 1, according to some embodiments.

FIG. 8 illustrates a switch fault detection process 800 usable to detect a switch fault in an apparatus configured to delivery negative pressure wound therapy, such as the TNP apparatus 11. For convenience, the switch fault detection process 800 is described in the context of the TNP apparatus 11, but may instead be implemented in other systems described herein or by other systems not shown. The switch fault detection process 800 can be performed, for example, by the control circuitry 12A alone or in combination with the user interface 12D. The process 800 can be used to detect a fault in the user interface 12D. The switch fault detection process 800 may begin, in some instances, with the negative pressure source 12C turned off and not providing negative pressure.

At block 802, the switch fault detection process 800 can detect a toggle in a state of one of a set of contacts. For example, the control circuitry 12A can detect a toggle in the state of one of the pair of contacts of the switch 21, such as the contacts 302 and 304 shown in FIG. 3A. The toggle can be detected, for instance, from a change in an electrical characteristic (such as voltage or current), mechanical characteristic, pressure characteristic, or thermal characteristic of the one of the pair of contacts of the switch 21 and may be detected using a sensor.

At block 804, the switch fault detection process 800 can determine whether a state of another set of contacts is toggled. For example, the control circuitry 12A can detect, in response to a user input to the switch 21, a toggle in the state of another of the pair of contacts of the switch 21, such as the contacts 306 and 308 shown in FIG. 3A. The toggle can be detected, for instance, from a change in an electrical characteristic (such as voltage or current), mechanical characteristic, pressure characteristic, or thermal characteristic of the other of the pair of contacts of the switch 21 and may be detected using a sensor.

If the state of the another set of contacts is toggled, the switch fault detection process 800 can move to block 806 and supply negative pressure. The supply of negative pressure can be initiated by the control circuitry 12A and performed by the negative pressure source 12C, and the negative pressure can be supplied to the wound dressing 13 via the fluid flow path.

If the state of the another set of contacts is not toggled, the switch fault detection process 800 can move to block 808 and output a switch fault indication. The failure of the another set of contacts to toggle can be indicative of the another set of contacts failing to toggle as would be expected from a user input. For example, the control circuitry 12A detect a switch fault from the another set of contacts not toggling and thus output the switch fault indication, such as for presentation on the user interface 12D. The switch fault detection process 800 at block 804 may moreover monitor for the toggle of the another set of contacts for a time period, such as 0.5 seconds, 1 second, 2 seconds, 3 second, 5 seconds, or longer, before moving to block 808 and outputting the switch fault indication.

Although the processes in FIGS. 7 and 8 describe toggling one or more contacts to enable or disable supply of negative pressure, toggling one or more contacts can be used for controlling other functions of the TNP apparatus 11, such as for example initial activation of the TNP apparatus 11.

Other Variations

Although one of more examples in this disclosure describe that a negative pressure source, control circuitry, or other components can be part of an integrated unit, such as on-board a wound dressing, the one or more examples do not limit the scope of the disclosure to such an integrated unit. The features related to redundant activation or deactivation control can, for instance, be included as part of a TNP apparatus that is not integral or separate from a wound dressing or with any medical or electronic device.

Any value of a threshold, limit, duration, etc. provided herein is not intended to be absolute and, thereby, can be approximate. In addition, any threshold, limit, duration, etc. provided herein can be fixed or varied either automatically or by a user. Furthermore, as is used herein relative terminology such as exceeds, greater than, less than, etc. in relation to a reference value is intended to also encompass being equal to the reference value. For example, exceeding a reference value that is positive can encompass being equal to or greater than the reference value. In addition, as is used herein relative terminology such as exceeds, greater than, less than, etc. in relation to a reference value is intended to also encompass an inverse of the disclosed relationship, such as below, less than, greater than, etc. in relations to the reference value. Moreover, although blocks of the various processes may be described in terms of determining whether a value meets or does not meet a particular threshold, the blocks can be similarly understood, for example, in terms of a value (i) being below or above a threshold or (ii) satisfying or not satisfying a threshold.

Features, materials, characteristics, or groups described in conjunction with a particular aspect, embodiment, or example are to be understood to be applicable to any other aspect, embodiment or example described herein unless incompatible therewith. All of the features disclosed in this specification (including any accompanying claims, abstract, and drawings), or all of the steps of any method or process so disclosed, may be combined in any combination, except combinations where at least some of such features or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

While certain embodiments have been described, these embodiments have been presented by way of example only, and are not intended to limit the scope of protection. Indeed, the novel methods and systems described herein may be embodied in a variety of other forms. Furthermore, various omissions, substitutions and changes in the form of the methods and systems described herein may be made. Those skilled in the art will appreciate that in some embodiments, the actual steps taken in the processes illustrated or disclosed may differ from those shown in the figures. Depending on the embodiment, certain of the steps described above may be removed, others may be added. For example, the actual steps or order of steps taken in the disclosed processes may differ from those shown in the figure. Depending on the embodiment, certain of the steps described above may be removed, others may be added. For instance, the various components illustrated in the figures may be implemented as software or firmware on a processor, controller, ASIC, FPGA, or dedicated hardware. Hardware components, such as processors, ASICs, FPGAs, and the like, can include logic circuitry. Furthermore, the features and attributes of the specific embodiments disclosed above may be combined in different ways to form additional embodiments, all of which fall within the scope of the present disclosure.

User interface screens illustrated and described herein can include additional or alternative components. These components can include menus, lists, buttons, text boxes, labels, radio buttons, scroll bars, sliders, checkboxes, combo boxes, status bars, dialog boxes, windows, and the like. User interface screens can include additional or alternative information. Components can be arranged, grouped, displayed in any suitable order.

Although the present disclosure includes certain embodiments, examples and applications, it will be understood by those skilled in the art that the present disclosure extends beyond the specifically disclosed embodiments to other alternative embodiments or uses and obvious modifications and equivalents thereof, including embodiments which do not provide all of the features and advantages set forth herein. Accordingly, the scope of the present disclosure is not intended to be limited by the specific disclosures of preferred embodiments herein, and may be defined by claims as presented herein or as presented in the future.

Conditional language, such as "can," "could," "might," or "may," unless specifically stated otherwise, or otherwise understood within the context as used, is generally intended to convey that certain embodiments include, while other embodiments do not include, certain features, elements, or steps. Thus, such conditional language is not generally intended to imply that features, elements, or steps are in any way required for one or more embodiments or that one or more embodiments necessarily include logic for deciding, with or without user input or prompting, whether these features, elements, or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, or 0.1 degree.

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

What is claimed:

1. An apparatus for applying negative pressure to a wound, the apparatus comprising:
   a negative pressure source configured to provide negative pressure to a wound dressing via a fluid flow path;
   a switch comprising an actuator configured to toggle a state of a first pair of electrical contacts and a state of a second pair of electrical contacts in response to a user input, the switch being configured to receive the user input as a depression of the switch; and
   control circuitry configured to:
      supply negative pressure with the negative pressure source in response to the first pair of electrical contacts being in an electrically connected state and the second pair of electrical contacts being in the electrically connected state, disable supply of negative pressure with the negative pressure source in response to the first pair of electrical contacts being in an electrically disconnected state and the second pair of electrical contacts being in the electrically disconnected state, and disable supply of negative pressure with the negative pressure source in response to the first pair of electrical contacts being in the electrically connected state and the second pair of electrical contacts being in the electrically disconnected state.

2. The apparatus of claim 1, wherein the actuator is configured to simultaneously toggle the state of the first pair of electrical contacts and the state of the second pair of electrical contacts in response to the user input.

3. The apparatus of claim 1, wherein the control circuitry is configured to supply negative pressure with the negative pressure source in response to no user inputs other than the user input to the switch.

4. The apparatus of claim 1, wherein when the actuator is broken and no longer able to toggle the state of the first pair of electrical contacts or the state of the second pair of electrical contacts, the control circuitry is further configured to no longer supply negative pressure with the negative pressure source.

5. An apparatus for applying negative pressure to a wound, the apparatus comprising:
   a negative pressure source configured to provide negative pressure to a wound dressing via a fluid flow path;
   a switch comprising an actuator configured to toggle a state of a first pair of electrical contacts and a state of a second pair of electrical contacts in response to a user input, the switch being configured to receive the user input as a depression of the switch; and
   control circuitry configured to:
      supply negative pressure with the negative pressure source in response to the first pair of electrical contacts being in an electrically connected state and the second pair of electrical contacts being in the electrically connected state,
      disable supply of negative pressure with the negative pressure source in response to the first pair of electrical contacts being in an electrically disconnected state or the second pair of electrical contacts being in the electrically disconnected state, and
      detect a switch fault in response to the state of the first pair of electrical contacts not toggling within a threshold period of time subsequent to toggling of the state of the second pair of electrical contacts.

6. The apparatus of claim 5, wherein the threshold period of time is between 0.5 seconds and 5 seconds.

7. The apparatus of claim 5, wherein the control circuitry is further configured to output a switch fault indication in response to detection of the switch fault.

8. The apparatus of claim 1, wherein the first pair of electrical contacts comprises a plurality of first traces and the second pair of electrical contacts comprises a plurality of second traces, and the actuator is configured to, in response to the user input, short the plurality of first traces to one another and short the plurality of second traces to one another.

9. The apparatus of claim 1, wherein the negative pressure source is disposed on or within the wound dressing.

10. The apparatus of claim 1, wherein the control circuitry is configured to disable supply of negative pressure with the negative pressure source by deactivation of operation of the negative pressure source, opening of a vent positioned in the fluid flow path, or closing of a valve positioned in the fluid flow path.

11. A method for controlling application of negative pressure to a wound, the method comprising:
   using an actuator of a switch, toggling a first pair of electrical contacts from an electrically disconnected state to an electrically connected state and a second pair of electrical contacts from the electrically disconnected state to the electrically connected state in response to receipt of a first user input to the switch as a depression of the switch;
   supplying negative pressure with a negative pressure source to a wound dressing via a fluid flow path when the first pair of electrical contacts is in the electrically connected state and the second pair of electrical contacts is in the electrically connected state; and
   changing the first pair of electrical contacts from the electrically connected state to the electrically disconnected state but not changing the second pair of electrical contacts from the electrically connected state to the electrically disconnected state; and
   disabling supply of negative pressure with the negative pressure source when the first pair of electrical contacts is in the electrically disconnected state and the second pair of electrical contacts is in the electrically connected state.

12. The method of claim 11, wherein said disabling supply of negative pressure comprises deactivating the negative pressure source.

13. The method of claim 11, wherein said supplying negative pressure is ended by said disabling supply of negative pressure.

14. The method of claim 11, wherein said toggling the first pair of electrical contacts and the second pair of electrical contacts comprises simultaneously toggling the first pair of electrical contacts and the second pair of electrical contacts.

15. The method of claim 11, further comprising detecting a switch fault in response to the first pair of electrical contacts not changing between the electrically connected state and the electrically disconnected state within a threshold period of time subsequent to the second pair of electrical contacts changing between the electrically connected state and the electrically disconnected state.

16. The method of claim 15, wherein the threshold period of time is between 0.5 seconds and 5 seconds.

17. The method of claim 15, further comprising outputting a switch fault indication for presentation to a user in response to said detecting the switch fault.

18. The method of claim 11, wherein said disabling supply of negative pressure comprises opening of a vent positioned in the fluid flow path or closing of a valve positioned in the fluid flow path.

19. The apparatus of claim 5, wherein when the actuator is broken and no longer able to toggle the state of the first pair of electrical contacts or the state of the second pair of electrical contacts, the control circuitry is further configured to no longer supply negative pressure with the negative pressure source.

20. The apparatus of claim 5, wherein the first pair of electrical contacts comprises a plurality of first traces and the second pair of electrical contacts comprises a plurality of second traces, and the actuator is configured to, in response to the user input, short the plurality of first traces to one another and short the plurality of second traces to one another.

* * * * *